(12) United States Patent
Loffredo et al.

(10) Patent No.: US 11,351,071 B2
(45) Date of Patent: Jun. 7, 2022

(54) TAMPON DISPENSING DEVICES AND METHODS FOR USING THE SAME

(71) Applicant: Huge, LLC, Brooklyn, NY (US)

(72) Inventors: Stephanie Loffredo, Washington, DC (US); Zachary Chase Saale, Washington, DC (US)

(73) Assignee: Huge, LLC, Brooklyn, NY (US)

( * ) Notice: Subject to any disclaimer, the term of this patent is extended or adjusted under 35 U.S.C. 154(b) by 283 days.

(21) Appl. No.: 16/806,643

(22) Filed: Mar. 2, 2020

(65) Prior Publication Data

US 2021/0267823 A1    Sep. 2, 2021

(51) Int. Cl.
*A61F 15/00* (2006.01)
*B65D 83/00* (2006.01)
*G07F 17/00* (2006.01)

(52) U.S. Cl.
CPC ........ *A61F 15/003* (2013.01); *B65D 83/0005* (2013.01); *G07F 17/00* (2013.01)

(58) Field of Classification Search
CPC .... A61F 15/003; B65D 83/0005; G07F 17/00
See application file for complete search history.

(56) References Cited

U.S. PATENT DOCUMENTS

| 5,555,965 | A | * | 9/1996 | Mishina | A61F 15/003 194/217 |
| 9,501,888 | B1 | * | 11/2016 | Morad | G08B 21/182 |
| 11,141,328 | B1 | * | 10/2021 | Morad | A47F 1/10 |
| 11,185,453 | B2 | * | 11/2021 | Morad | A61F 15/003 |
| 2011/0266300 | A1 | * | 11/2011 | Schwarzli | G07F 11/005 221/133 |
| 2015/0182006 | A1 | * | 7/2015 | Blaze | A45D 44/005 700/233 |
| 2018/0327181 | A1 | * | 11/2018 | Moore | A61F 13/5516 |

* cited by examiner

*Primary Examiner* — Michael Collins
(74) *Attorney, Agent, or Firm* — Byrne Poh LLP

(57) ABSTRACT

Tampon dispensing devices and methods for using the same are provided. In some embodiments, a tampon dispensing device includes a display that presents one or more codes for receiving a tampon, an actuator that is connected to a spindle structure that dispenses the tampon from a plurality of tampons stored in a storage unit, and a controller that is connected to the display and the actuator, where the controller is configured to: receive, from a server, a code for dispensing one of the plurality of tampons; present the received code on the display; receive, from the server, a request to dispense one of the plurality of tampons from the storage unit; and transmit an instruction to the actuator that causes the actuator to rotate a spindle structure such that the tampon is dispensed from the storage unit into a dispensing area.

20 Claims, 12 Drawing Sheets

TAMPON DISPENSING DEVICES AND METHODS FOR USING THE SAME

TECHNICAL FIELD

The disclosed subject matter relates to tampon dispensing devices and methods for using the same.

BACKGROUND

Many restrooms include coin-operated vending machines that dispense tampons and other feminine hygiene products. Such a vending machine typically includes a slot for accepting a coin (e.g., one or more quarters). Upon inserting the requisite number of coins into the slot, a pushbutton, a rotatable lever, or other mechanical knob of the vending machine is then mechanically activated and can be used to forcibly move a tampon out of a storage holder and into a tray.

These vending machines, unfortunately, suffer from a number of issues. First, it is cumbersome for purchasers to carry coins and, in many instances, it is rare to have the exact amount needed to dispense a tampon using the coin slot. Second, in many instances, there are mechanical issues that often occur with these vending machines. For example, the slot on a vending machine may not be accepting coins (e.g., due to a jammed coin slot). In another example, while the slot on a vending machine may be accepting coins, the vending machine may not be registering that a coin has been inserted. In yet another example, the pushbutton on a vending machine may be inoperative such that a tampon is not dispensed in response to pressing the pushbutton (e.g., the pushbutton is not mechanically activated upon inserting the payment in the coin slot, the pushbutton is mechanically activated but a tampon is jammed in the storage holder such that it cannot be moved into the tray, etc.). Moreover, in addition to the mechanical issues noted above, it can be difficult to maintain one or more of these vending machines. For example, it may be difficult for a maintenance staff member to know when these coin-operated vending machines are either low in stock or out of stock.

As such, when a tampon or other feminine hygiene product is needed, it is often found that these coin-operated vending machines are inoperable, thereby leaving women without access to tampons in many public restrooms.

Accordingly, it is desirable to provide new tampon dispensing devices and methods for using the same.

SUMMARY

In accordance with various embodiments of the disclosed subject matter, tampon dispensing devices and methods for using the same are provided.

In accordance with some embodiments of the disclosed subject matter, a tampon dispensing device is provided that includes: a display that presents one or more codes for receiving a tampon; an actuator that is connected to a spindle structure that dispenses the tampon from a plurality of tampons stored in a storage unit; and a controller that is connected to the display and the actuator, wherein the controller is configured to: receive, from a server, a code for dispensing one of the plurality of tampons; present the received code on the display; receive, from the server, a request to dispense one of the plurality of tampons from the storage unit; and transmit an instruction to the actuator that causes the actuator to rotate the spindle structure such that the tampon is dispensed from the storage unit into a dispensing area.

In some embodiments, the display is an electronic paper display.

In some embodiments, the received code is a phrase comprising a plurality of words.

In some embodiments, the controller is further configured to present the received code and a phone number for transmitting the received code to dispense one of the plurality of tampons.

In some embodiments, the actuator further comprises a stepper motor that is connected to a drive shaft, wherein the drive shaft is connected to the spindle structure that is holding the tampon, wherein the instruction causes the stepper motor to rotate the drive shaft by a particular rotation amount, and wherein the rotation of the draft shaft causes the spindle structure to rotate to dispense the tampon from the spindle structure to the dispensing area.

In some embodiments, the drive shaft is connected to a central portion of the spindle structure.

In some embodiments, the spindle structure includes a recessed portion for receiving an individual tampon from the storage unit.

In some embodiments, the tampon dispensing device further comprises a funnel between the storage unit and the dispensing area, wherein the funnel includes the spindle structure and one or more aligners that cause the individual tampon to be placed from the storage unit to the recessed portion of the spindle structure.

In some embodiments, the tampon dispensing device further comprises a funnel between the storage unit and the dispensing area, wherein the funnel includes the spindle structure and one or more aligners that cause the individual tampon to be released from the recessed portion of the spindle structure to the dispensing area.

In some embodiments, the tampon dispensing device further comprises a door that includes a window for viewing at least a portion of the plurality of tampons in the storage unit.

In some embodiments, the tampon dispensing device further comprises a network interface that is connected to the controller, wherein the controller is further configured to: transmit, to the server via the network interface, a request for the code to dispense one of the plurality of tampons; and receive, from the server via the network interface, the code responsive to the request.

In some embodiments, the controller is further configured to detect that the device is in an active state and, in response to detecting that the device is in the active state, the request for the code is transmitted to the server via the network interface.

In some embodiments, the controller is further configured to determine that a predetermined amount of time has elapsed in which one of the plurality of tampons has not been dispensed and transmit a request to the server for an updated code to present on the display for dispensing one of the plurality of tampons.

In some embodiments, the controller is further configured to transmit a request to the server for an updated code to present on the display for dispensing a next tampon from the plurality of tampons in response to dispensing the tampon from the storage unit into the dispensing area.

In some embodiments, the tampon dispensing device further comprises a sensor that detects whether the tampon was dispensed from the storage unit into the dispensing area, wherein the sensor is connected to the controller and wherein the controller is further configured to determine whether the tampon was properly dispensed into the dispensing area based on sensor data from the sensor.

In some embodiments, the controller is further configured to transmit an alert notification in response to determining that the tampon was not properly dispensed.

In some embodiments, the controller is further configured to enter a maintenance mode in which device error information that at least includes the sensor data is transmitted to a maintenance account.

In some embodiments, the sensor is a through-beam sensor that emits a beam within the dispensing area of the tampon dispensing device.

In some embodiments, the tampon dispensing device further comprises a sensor that detects whether the plurality of tampons stored in the storage unit is less than a predetermined amount, wherein the sensor is connected to the controller and wherein the controller is further configured to transmit an alert notification in response to determining that the plurality of tampons stored in the storage unit is less than the predetermined amount.

In some embodiments, the sensor is a through-beam sensor that emits a beam at a particular level within the storage unit of the tampon dispensing device.

In accordance with some embodiments of the disclosed subject matter, a method for dispensing tampons is provided, the method comprising: providing a tampon dispensing device that includes: a display that presents one or more codes for receiving a tampon; an actuator that is connected to a spindle structure that dispenses the tampon from a plurality of tampons stored in a storage unit; and a controller that is connected to the display and the actuator; receiving, from a server, a code for dispensing one of the plurality of tampons; presenting the received code on the display; receiving, from the server, a request to dispense one of the plurality of tampons from the storage unit; and transmitting an instruction to the actuator that causes the actuator to rotate the spindle structure such that the tampon is dispensed from the storage unit into a dispensing area.

In accordance with some embodiments of the disclosed subject matter, a system for dispensing tampons is provided, the system comprising: means for receiving, from a server, a code for dispensing one of a plurality of tampons; means for presenting the received code on a display of a tampon dispensing device; means for receiving, from the server, a request to dispense one of the plurality of tampons from a storage unit of the tampon dispensing device; and transmitting an instruction to the actuator of the tampon dispensing device that causes the actuator to rotate a spindle structure such that the tampon is dispensed from the storage unit into a dispensing area of the tampon dispensing device.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

In accordance with various embodiments of the disclosed subject matter, tampon dispensing devices and methods for using the same are provided.

Generally speaking, a tampon dispensing device is provided in which a code can be presented on a display of the tampon dispensing device. The display can prompt a user of the tampon dispensing device to transmit a communication message using a computing device of the user, where the message includes the presented code to receive a tampon from the tampon dispensing device. In a more particular example, the user can transmit a text message that includes a code including two randomly selected words being presented on the display of the tampon dispensing device to a phone number that is also presented on the display of the tampon dispensing device. In response to determining that the code in the message matches the code presented on the display of the tampon dispensing device, the tampon dispensing device can receive a dispensing instruction that causes an actuator to dispense a tampon from a storage unit (e.g., a hopper that stores multiple tampons) to a reception area.

Figure 1:
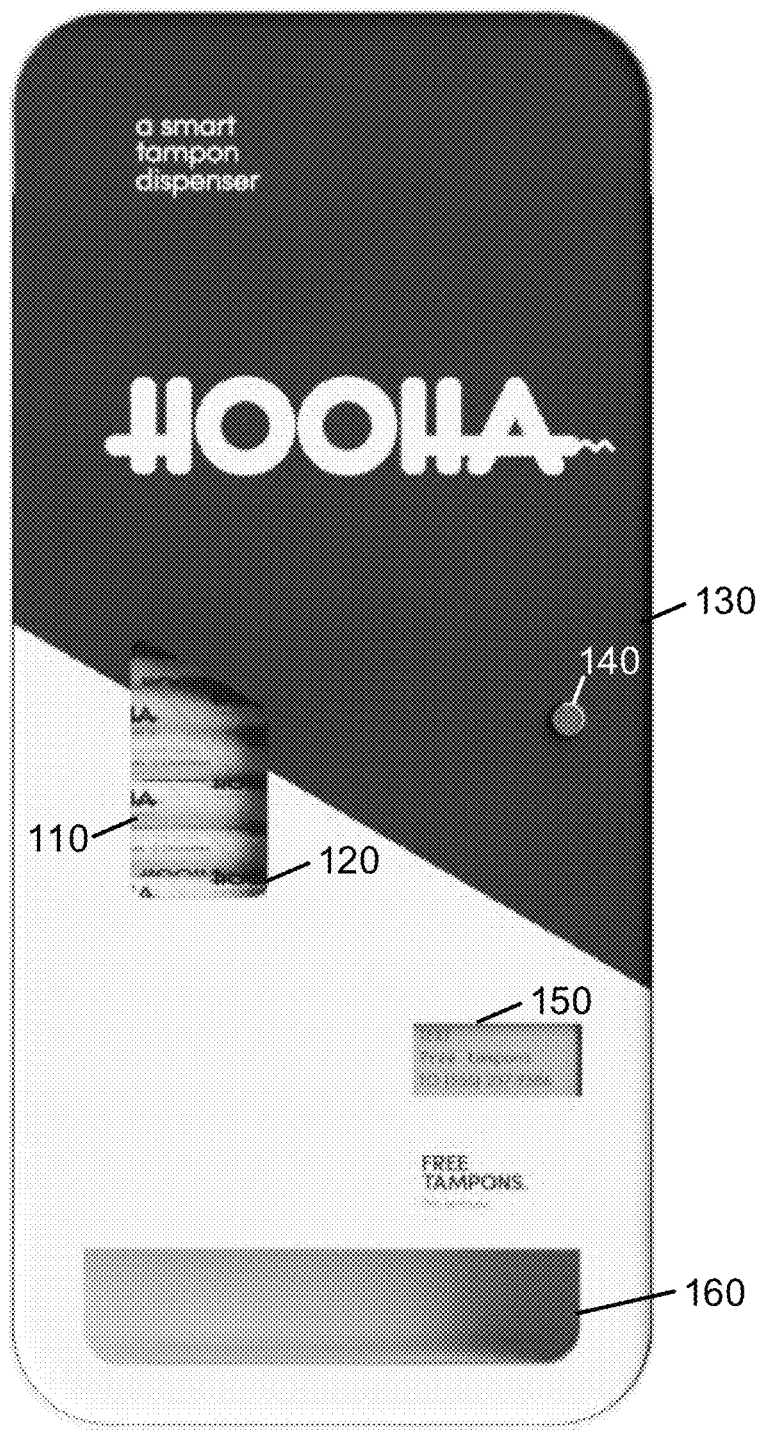
FIG. 1 shows an illustrative example of an exterior portion of a tampon dispensing device in accordance with some embodiments of the disclosed subject matter.

For example, as shown in FIG. 1, a tampon dispensing device 100 that is installed in a restroom can include multiple tampons 110 stored within tampon dispensing device 100. The availability of tampons in tampon dispensing device 100 can be seen through a window 120 of device door 130 that is placed to allow a user of tampon dispensing device 100 or a facility manager of tampon dispensing device 100 to view at least a portion of the contents of a storage unit of tampon dispensing device 100 (e.g., a hopper assembly that is configured to hold multiple tampons or other feminine hygiene products). In continuing this example, tampon dispensing device 100 can include a display 150, such as an electronic paper display, that prompts a user of tampon dispensing device 100 to transmit a communication message that includes a particular code to a particular phone number. As shown in FIG. 1, display 150 can prompt the user of tampon dispensing device 100 to transmit a text message (e.g., "TEXT" on display 150) that includes the code "FREE TAMPONS" presented on display 150 to the phone number "555-237-9586" that is also presented on display 150 using a mobile computing device of the user. In response to determining that the code in the transmitted text message (e.g., "FREE TAMPONS" in the message) matches the code presented on display 150 (e.g., "FREE TAMPONS" on display 150), tampon dispensing device 100 can receive a dispensing instruction to dispense one of the tampons 110 to the user.

In some embodiments, the tampon dispensing device can include a controller that controls the operation of the tampon dispensing device. The controller can, for example, request a code for dispensing one of the multiple tampons stored in the storage unit, receive the code for dispensing one of the multiple tampons, request an updated code for dispensing one of the multiple tampons stored in the storage unit in response to determining that a particular amount of time has elapsed since the presentation of a current code on the display, request an updated code for dispensing one of the multiple tampons stored in the storage unit in response to determining that a previously presented code was used to dispense a tampon, etc. In another example, the controller of the tampon dispensing device can be used to transmit instructions to motion components of the tampon dispensing device, such as an actuator that causes a tampon to be dispensed from a storage unit to a reception area. In yet another example, the controller of the tampon dispensing device can be used to receive sensor data from one or more sensors in the tampon dispensing device, where suitable actions can be performed based on the sensor data (e.g., transmit a notification that a tampon has been properly dispensed into the dispensing area, transmit a notification that a tampon is jammed or has otherwise not been dispensed into the dispensing area, transmit a notification that the storage unit holding one or more tampons is low and should be refilled, etc.).

In some embodiments, the tampon dispensing device can include an actuator for dispensing a tampon from the storage unit and to the reception area, where a user of the tampon dispensing device can receive the tampon. For example, the actuator can include a stepper motor and a drive shaft, where the drive shaft is connected to a spindle structure. In continuing this example, the spindle structure can include a recessed portion that is configured to receive an individual tampon from the storage unit. When the stepper motor causes the drive shaft to rotate, the spindle structure rotates from a first position in which the individual tampon is held in the recessed portion of the spindle structure to a second position in which the individual tampon is released from the recessed portion of the spindle structure and into the reception area of the tampon dispensing device.

In some embodiments, the tampon dispensing device can include one or more sensors. For example, the tampon dispensing device can include a sensor that detects whether a tampon was properly dispensed to the dispensing area. In a more particular example, the sensor can be a beam-through sensor that emits an infrared beam at a particular position at or near the dispensing area, where the controller can determine that a tampon was dispensed by the tampon dispensing device by detecting, from the sensor data, that the infrared beam was disrupted. In another example, the tampon dispensing device can include a sensor that detects whether the storage unit should be refilled with additional tampons. In a more particular example, the sensor can be a beam-through sensor that emits an infrared beam at a particular position within the storage unit of the tampon dispensing device, where the controller can determine that the storage unit should be refilled by detecting that the infrared beam is not being disrupted by the contents of the storage unit (e.g., the stock is lower than a particular level).

Note that, although the embodiments described herein generally relate to dispensing a tampon, this is merely illustrative and the dispensing device can be used to dispense any suitable product. For example, in some embodiments, the dispensing component in the tampon dispensing device (e.g., configured to include the storage unit and the spindle structure that aids in dispensing an individual tampon from the storage unit to the reception area) can be removed and replaced with a different dispensing component for dispensing any other suitable product (e.g., sanitary pads, over-the-counter medication, etc.).

These and other features of the tampon dispensing device are further described in connection with FIGS. 1-12.

Turning to FIG. 1, an illustrative example of an exterior portion of a tampon dispensing device 100 is shown in accordance with some embodiments of the disclosed subject matter.

In some embodiments, tampon dispensing device 100 can include a device door 130 having multiple windows. For example, as shown in FIG. 1, device door 130 of tampon dispensing device 100 can include a window 120 that is positioned to allow a user of tampon dispensing device 100 or a facility manager of tampon dispensing device 100 to view at least a portion of the contents of a storage unit of tampon dispensing device 100 (e.g., a hopper assembly that is configured to hold multiple tampons or other feminine hygiene products). In continuing this example, window 120 can provide a user of tampon dispensing device 100 with an opportunity to determine whether tampon dispensing device 100 has any tampons 110 for dispensing and/or can provide a facility manager with an opportunity to determine the stock level of a storage unit of tampon dispensing device 100. In another example, as also shown in FIG. 1, device door 130 of tampon dispensing device 100 can include a window 150 that is positioned to allow a user of tampon dispensing device 100 or a facility manager of tampon dispensing device 100 to view a display associated with tampon dispensing device, such as an electronic paper display. In continuing this example, window 150 can provide a user of tampon dispensing device 100 with an opportunity to receive instructions for transmitting a suitable message that causes tampon dispensing device 100 to dispense a tampon (e.g., send a text message to receive a free tampon).

It should be noted that window 120 and window 150 can be any suitable size and can be positioned at any suitable location on device door 130 of tampon dispensing device 100. For example, window 120 can be configured to allow the entire contents of a storage unit of tampon dispensing device to be visible to a user. In another example, window 120 can be configured to allow a particular number of tampons at the bottom of the storage unit to be visible to a user (e.g., to show the last five tampons that are available for dispensing). In yet another example, window 150 can be configured to be a particular size and position such that a particular portion of the electronic paper display is visible from the exterior portion of tampon dispensing device 100. In continuing this example, the electronic paper display can include a first region that is visible from the exterior portion of tampon dispensing device 100 through window 150 and that includes instructions for dispensing a tampon and a second region that is visible upon opening device door 130 and that includes device information for a facility manager of tampon dispensing device 100 (e.g., an error message, a number of tampons dispensed, etc.).

In some embodiments, tampon dispensing device 100 can include a cut-out portion 160 such that a user can access the reception area for receiving a dispensed tampon. Additionally or alternatively to cut-out portion 160, tampon dispensing device 100 can include a door for receiving a dispensed tampon. For example, the door can be an electronically actuated door that automatically opens in response to detecting that a tampon has been dispensed into the reception area. In another example, the door can be electronically actuated to automatically open in response to transmitting an actuation instruction to the actuation components of tampon dispensing device 100 (e.g., each time a dispense instruction is sent to the actuator, the door is unlocked and/or opened to provide access to the reception area). In yet another example, the door can be automatically unlocked in response to transmitting an actuation instruction to the actuation components of tampon dispensing device 100.

In some embodiments, tampon dispensing device 100 can include a lock 140 (e.g., a digital lock, a vending machine lock, or any other suitable type of lock) that can allow device door 130 of tampon dispensing device to be opened by an authorized user of tampon dispensing device 100 (and, therefore, provide access to internal components of tampon dispensing device for troubleshooting a device error and/or the storage unit of tampon dispensing device 100 for restocking the storage unit with tampons).

In some embodiments, internal components of tampon dispensing device 100 can be accessed upon opening device door 130. An illustrative example of an interior portion of a tampon dispensing device in accordance with some embodiments of the disclosed subject matter is shown in FIG. 2.

Figure 2:
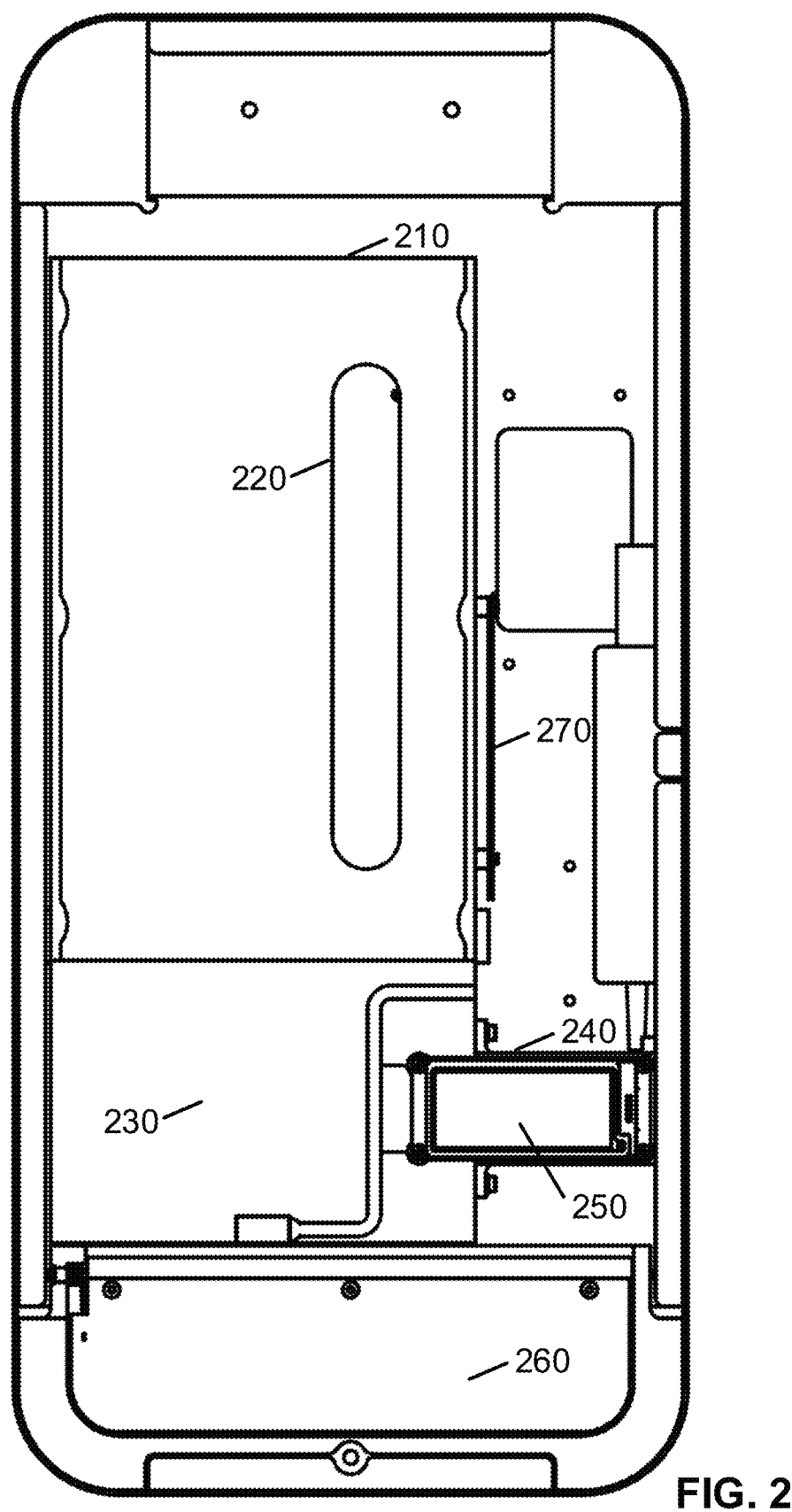
FIG. 2 shows an illustrative example of an interior portion of a tampon dispensing device in accordance with some embodiments of the disclosed subject matter.

As shown in FIG. 2, tampon dispensing device 100 can include a storage unit 210 that is configured to hold one or more tampons. For example, storage unit 210 can be configured to hold fifty tampons (that may be contained in tubular packaging) in a vertically stacked arrangement.

It should be noted that storage unit 210 can be configured to hold any suitable number of tampons.

It should also be noted that storage unit 210 can be configured to receive tampons in any suitable manner. For example, a facility manager can open storage unit 210 and individually insert tampons one-by-one into storage unit 210. In another example, facility manager can open storage unit 210 and insert a cartridge that loads a particular number of tampons into storage unit 210 of tampon dispensing device 100. In yet another example, storage unit 210 can include a funnel structure that, upon placing one or more tampons into the funnel structure, causes the tampons to be loaded into storage unit 210 of tampon dispensing device 100 (e.g., orients each tampon into a vertically stacked arrangement).

As described above in connection with FIG. 1, tampon dispensing device 100 can include a window 120 that allows a user to view at least a portion of the contents of storage unit 210. In turn, as shown in FIG. 2, storage unit 210 can include a window 220 that aligns with window 120 on device door 130. This arrangement of window 120 and window 220 is also shown, for example, in FIG. 5. This window arrangement can, for example, allow a user to view at least a portion of the tampons contained within storage unit 210. It should be noted that window 120 of device door 130 and window 220 of storage unit 210 can provide different information to users—e.g., window 120 of device door 130 can provide a visual indication as to whether tampon dispensing device 100 include any tampons available for dispensing, while window 220 of storage unit 210 that can be accessed upon opening device door 130 can provide a visual indication as to whether storage unit 210 should be refilled or restocked with one or more tampons. It should also be noted that, in some embodiments, window 120 of device door 130 may not be aligned with window 220 of storage unit 210, where storage unit 210 is composed of a transparent material and window 120 of device door provides a visual indication as to whether any tampons are available for dispensing.

In some embodiments, the tampon dispensing device can include a dispensing unit 220 that dispenses a tampon from storage unit 210 to a reception area 260. For example, dispensing unit 220 can include a spindle structure that receives an individual tampon from storage unit 220 and, upon rotation from an upward position to a downward position, releases the individual tampon into reception area 260.

Figure 3:
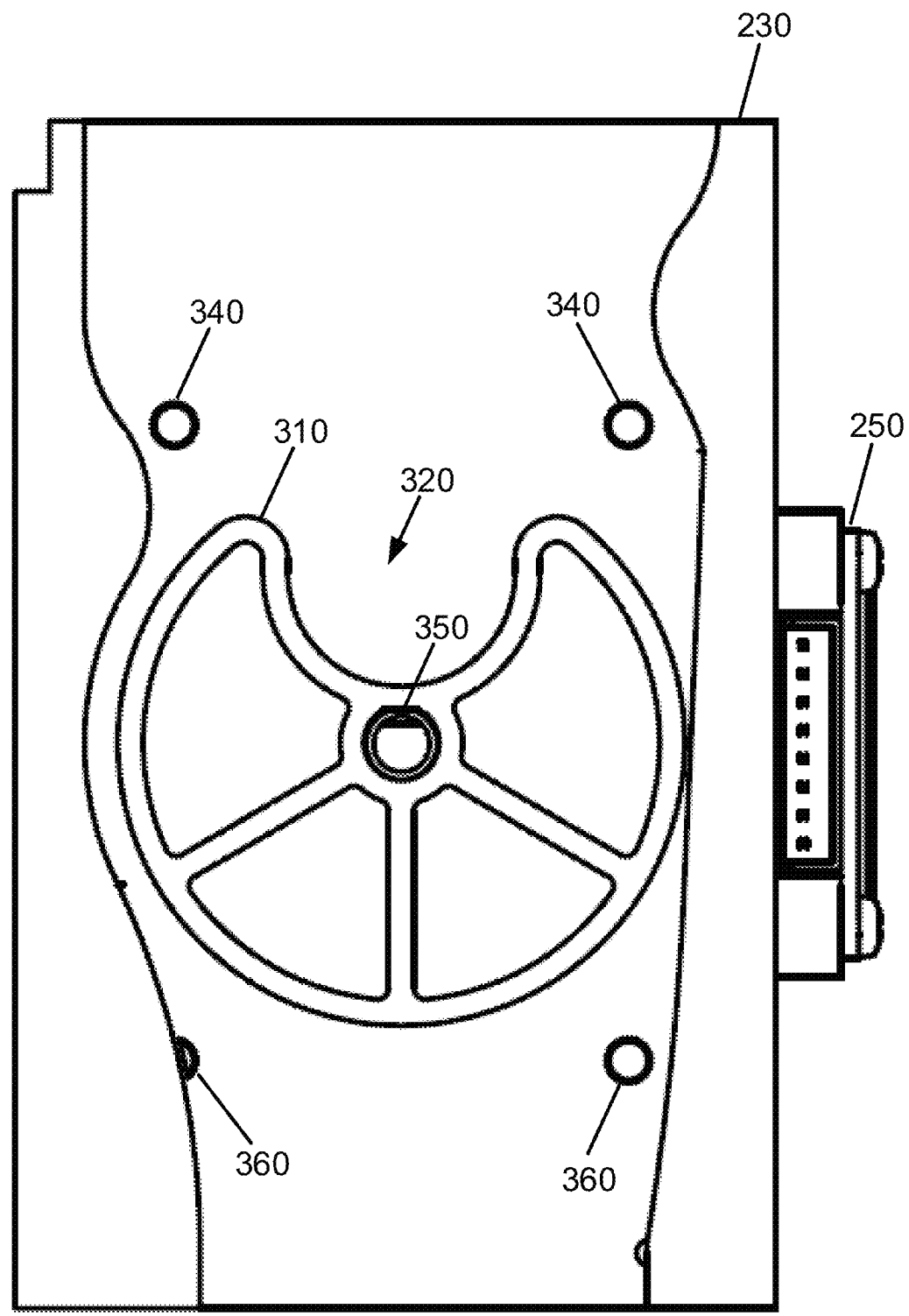
FIG. 3 shows a cross-sectional view of a spindle structure that holds a tampon for dispensing, where the spindle structure is positioned between a storage unit of a tampon dispensing device and a reception area of the tampon dispensing device, in accordance with some embodiments of the disclosed subject matter.

A cross-sectional view of dispensing unit 220 is shown, for example, in FIG. 3. As shown in FIG. 3, an individual tampon can be directed from storage unit 220 and into spindle structure 310 within dispensing unit 220. Spindle structure 310 can be a C-shaped structure that includes a recessed portion 320 that is configured to hold the individual tampon.

In some embodiments, dispensing unit 220 can include aligners 340 that assist the transport of the individual tampon from storage unit 220 and into recessed portion 320 of spindle structure 310. Aligners 340 can, for example, inhibit the individual tampon from being jammed in spindle structure 310 or any other component within dispensing unit 220. Aligners 340 can also, for example, inhibit multiple tampons from being directed into recessed portion 320 of spindle structure 310.

In some embodiments, recessed portion 320 can hold an individual tampon and, upon spindle structure 310 rotating in which recessed portion 320 moves from an upward position to a downward position, the individual tampon can be released from recessed portion 320 and into reception area 260. As described further in connection with FIGS. 5 and 6, a drive shaft can be connected to a central portion 350 of spindle structure 310, where the drive shaft can be connected to an actuator, such as a stepper motor. In response to the motor receiving an actuation instruction, the motor can cause the drive shaft to turn, which can cause spindle structure 310 to rotate—e.g., rotate from an initial position in which recessed portion 320 is in an upward position to a downward position.

In some embodiments, dispensing unit 220 can also include aligners 360 that assist the transport of the individual tampon from recessed portion 320 of spindle structure 310 and into reception area 260. Aligners 360 can, for example, inhibit the individual tampon from being jammed in spindle structure 310 or any other component within dispensing unit 220.

Figure 4:
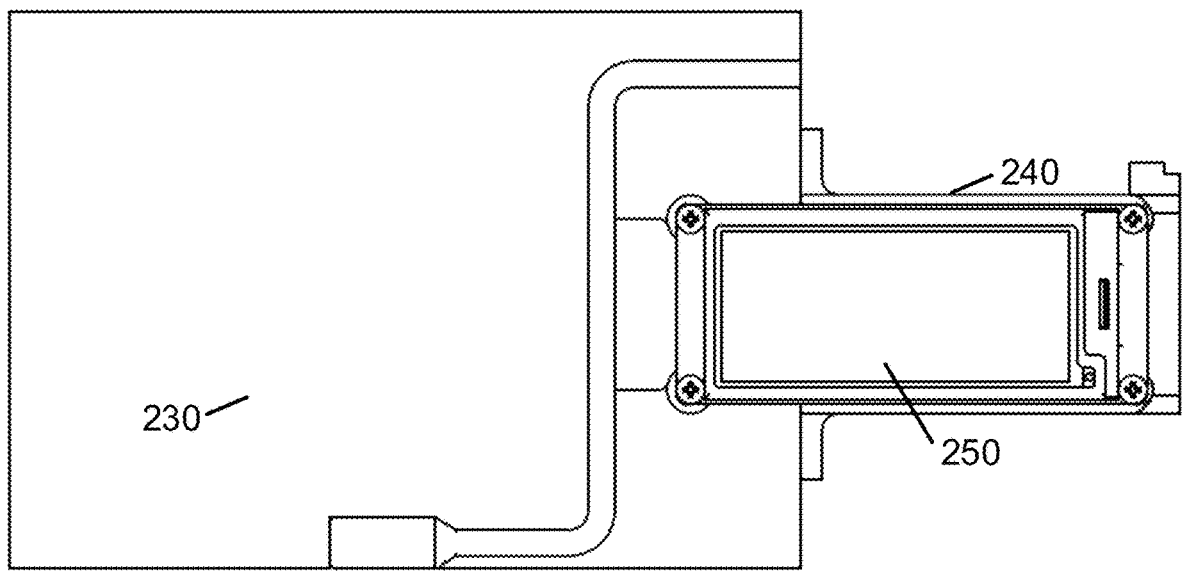
FIG. 4 shows an enlarged view of a display portion of a tampon dispensing device, where the display portion is mounted proximal to actuator components that dispense a tampon from a storage unit of the tampon dispensing device, in accordance with some embodiments of the disclosed subject matter.

An enlarged view of dispensing unit 220 is shown, for example, in FIG. 4. As shown in FIGS. 2, 3, and 4, a display 250 can be attached to dispensing unit 220. Display 250 can be any suitable screen on which tampon dispensing information and/or device information can be presented. For example, as described above, display 250 can present information to a user of tampon dispensing device 100, where the information provides instructions to transmit a text message using a mobile device that causes tampon dispensing device 100 to dispense a tampon. In some embodiments, display 250 can be any suitable type of screen or display, such as an electronic paper display, an LCD display, a touchscreen, and/or any other suitable type of screen or display.

Figure 5:
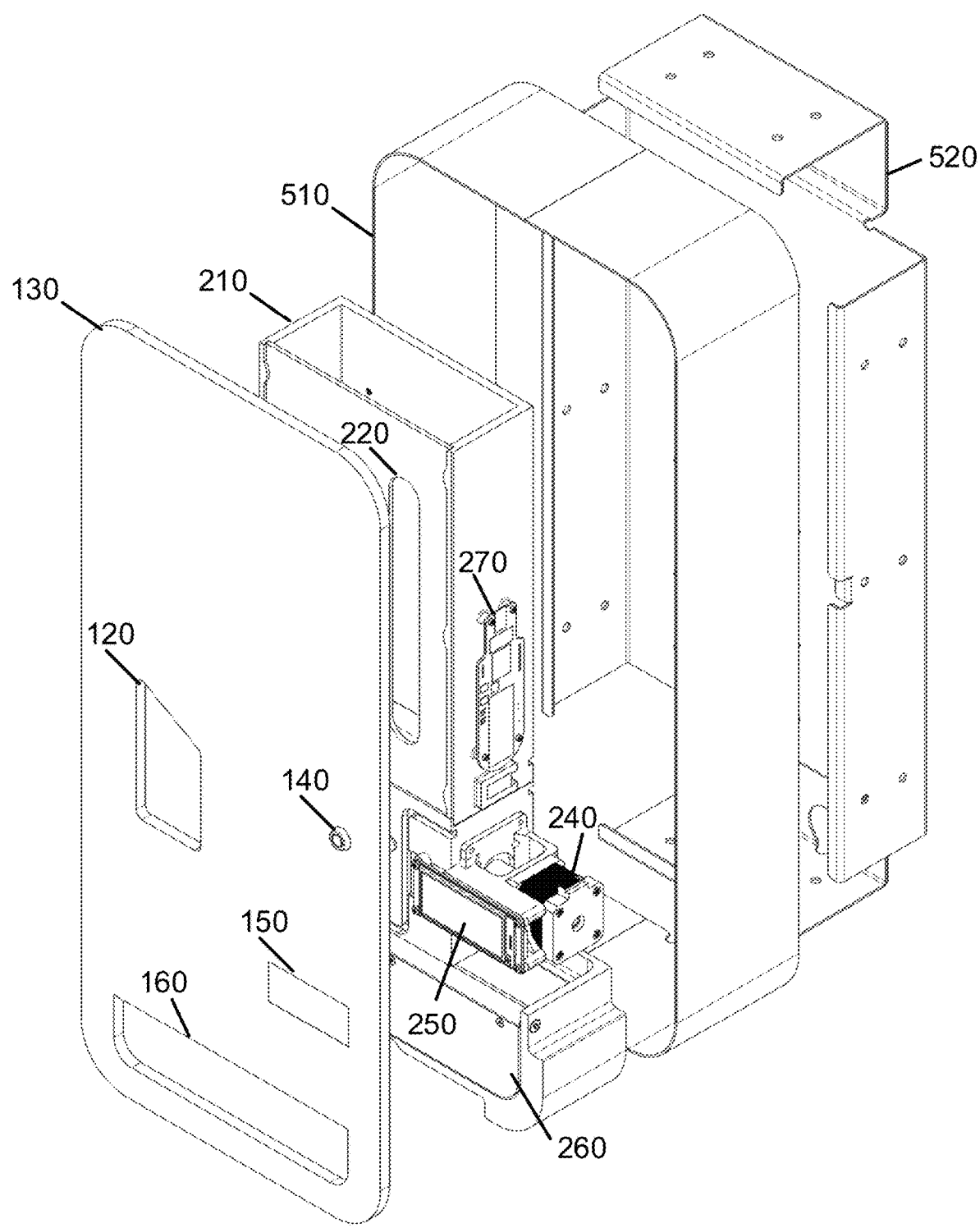
FIG. 5 shows a front perspective view of a tampon dispensing device in accordance with some embodiments of the disclosed subject matter.

It should be noted that, in some embodiments, actuator components 240 can be mounted to display 250. For example, as shown in FIGS. 2, 3, 4, and 5, an actuator, such as a stepper motor, can be mounted behind display 250. In a more particular example, FIG. 5 shows a perspective view of tampon dispensing device 100. In continuing this example, a drive shaft connected to the stepper motor 240 can extend into central portion 350 of spindle structure 310 that is within dispensing unit 220.

Referring back to FIG. 2, in some embodiments, tampon dispensing device 100 can include a controller 270. For example, controller 270 can be used to transmit an instruction to a stepper motor. In another example, controller 270 can be used to transmit an instruction to stepper motor controller that controls stepper motor, drive shaft, and/or other motion output components. It should be noted that controller 270 can include any suitable hardware processor, such as a microprocessor, a micro-controller, digital signal processor(s), dedicated logic, and/or any other suitable circuitry for controlling the functioning of a general purpose computer or a special purpose computer in some embodiments. In some embodiments, controller 270 can be controlled by a computer program stored in memory and/or storage of tampon dispensing device 100. For example, the computer program can cause controller 270 to receive an instruction to dispense a tampon, to transmit an actuation instruction to a stepper motor or other actuation components, to determine whether a tampon was dispensed into a reception area, to determine whether a storage unit has a particular number of tampons available for dispensing, and/or perform any other suitable actions.

In some embodiments, controller 270 can include a network interface component. For example, the network interface component can be used to associate tampon dispensing device 100 with a communications network so that it can communicate with a server for receiving dispensing instructions, for communicating with an administrative user, etc.

As shown in FIGS. 2 and 5, controller 270 can be mounted to a portion of storage unit 210. It should be noted that controller 270 can be positioned at any suitable location within tampon dispensing device 100.

Figure 6:
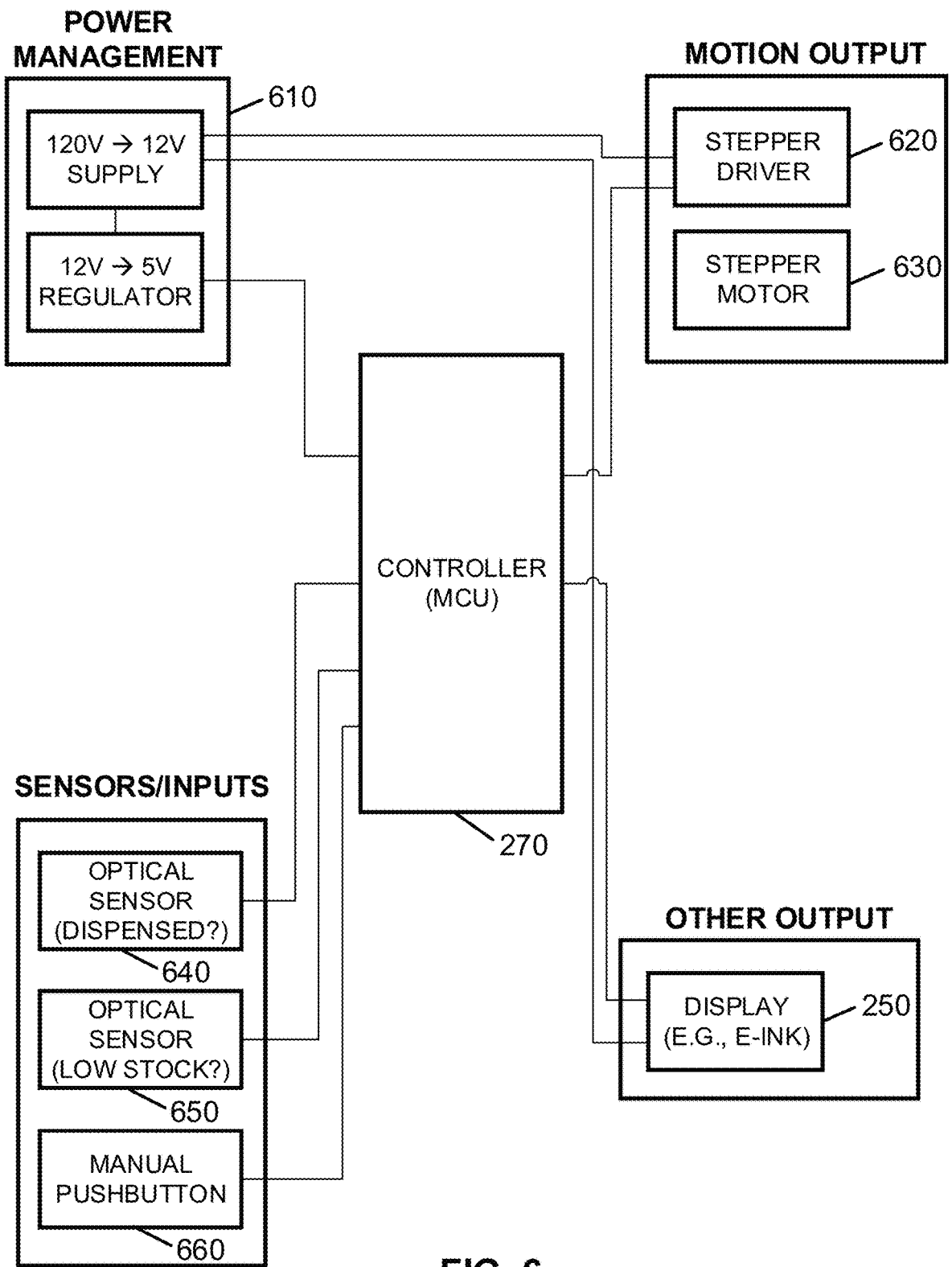
FIG. 6 shows an illustrative schematic diagram of the circuitry used in a tampon dispensing device that includes a controller, power management components, motion output components, display components, and sensor/input components in accordance with some embodiments of the disclosed subject matter.

Turning to FIG. 6, FIG. 6 shows an illustrative hardware schematic of tampon dispensing device 100 in accordance with some embodiments of the disclosed subject matter. As shown, controller 270 can be connected to power management components 610, motion output components (e.g., a stepper driver 620 and a stepper motor 630), other output components (e.g., a display 250), sensor components (e.g., an optical sensor 640 and an optical sensor 650), and input components (e.g., a manual pushbutton 660).

As described above, controller 270 can transmit instructions to motion output components, such as stepper driver 620 and stepper motor 630. For example, in response to receiving an instruction to dispense a tampon, controller 270 can transmit an instruction that causes an actuator (e.g., a stepper motor 630 connected to an actuator arm) to automatically rotate a spindle structure holding a tampon. In continuing this example, in response to detecting that a tampon has been dispensed into a reception area, controller 270 can transmit an instruction that causes an actuator (e.g., a stepper motor 630 connected to an actuator arm) to automatically rotate a spindle structure to receive a next tampon for dispensing.

It should be noted that tampon dispensing device 100 can include any suitable components to control the motion output components or actuator system, such as an instruction from a server to controller 270, where controller 270 transmits the instruction to stepper driver 620, stepper driver 620 transmits the instruction to a stepper motor controller, stepper motor controller transmits the instruction to stepper motor 630, and stepper motor 630 causes the spindle structure within the dispensing unit to move between different positions.

It should be noted that, although FIG. 6 shows multiple processing devices, such as controller 270 and stepper driver 620, this is merely illustrative. For example, in some embodiments, a single processing device can be used.

In some embodiments, tampon dispensing device 100 can include one or more power sources for providing power to one or more processing devices, one or more controller boards or other controller circuitry, one or more relay boards or other relay circuitry, etc. For example, in some embodiments, power management components 610 can include a power supply that provides power to each of the circuitry components of tampon dispensing device 100. In a more particular example, a power supply and/or power converter of power management components 610 can provide power to stepper driver 620, display 250 (e.g., an electronic paper display), and controller 270.

In some embodiments, tampon dispensing device 100 can receive sensor data from any suitable sensors.

For example, as shown in FIG. 6, an infrared through-beam sensor 640 having an emitter and a receiver or any other suitable photoelectric sensors can transmit an infrared light beam across a particular portion of tampon dispensing device 100 and can detect whether the infrared light beam has been disrupted. In continuing this example, infrared through-beam sensors 640 can be positioned at or near a reception area of tampon dispensing device 100. In turn, the detection that the infrared light beam has been disrupted can be correlated with an indication that a tampon has been dispensed into a reception area of tampon dispensing device 100. In order to determine whether a facility manager or other administrative user should be notified, tampon dispensing device 100 can determine that a particular amount of time has elapsed from the receipt of a dispense instruction (e.g., from a server) in which the infrared light beam has not been disrupted. Additionally or alternatively, the number of times that the infrared light beam has been disrupted can be correlated with the number of tampons that have been dispensed by tampon dispensing device 100. In order to determine whether tampon dispensing device 100 has been tampered with, tampon dispensing device 100 can compare the number of beam disruptions in a given period of times with the number of tampons in the storage unit.

In another example, as also shown in FIG. 6, an infrared through-beam sensor 650 having an emitter and a receiver or any other suitable photoelectric sensors can transmit an infrared light beam across a particular portion of tampon dispensing device 100 and can detect whether a storage unit of tampon dispensing device 100 should be refilled or restocked. In continuing this example, infrared through-beam sensor 650 can be positioned within a storage unit such that, when a tampon is no longer disrupting the infrared light beam, controller 270 can use the sensor data to transmit a notification that the storage unit of tampon dispensing device 100 should be refilled. In a more particular example, controller 270 can transmit a notification to an administrative user that states "There are less than five tampons left in the HOOHA™ on the first floor."

In some embodiments, tampon dispensing device 100 can include other input components, such as a manual pushbutton 660. For example, in response to display 250 indicating that a provided code matches the code associated with tampon dispensing device 100 and that a tampon is available for dispensing, display 250 can prompt a user of tampon dispensing device 100 to press manual pushbutton 660 to confirm an intent to receive a tampon. In another example, manual pushbutton 660 can be used to provide an alert to an administrative user, such as when tampon dispensing device 100 requires servicing, when tampon dispensing device 100 is low on stock or does not have any tampons available for dispensing, etc.

Although the embodiments described herein are related to dispensing an individual tampon in response to receiving a text message request that is relayed to a corresponding tampon dispensing device, it should be noted that any suitable product can be dispensed by device 100. For example, as shown in FIG. 5, door 130 can be attached to a device assembly 510, where storage unit 210, a dispensing unit, a reception area 260, and/or a stepper motor and other actuator components 240 are contained within device assembly 510. In continuing this example, device assembly 510 can be supported by a support structure 520 that allows tampon dispensing device 100 to be mounted to a wall (e.g., the wall of a public restroom). It should be noted that, to provide a device that dispenses a different product, storage unit 210 and a corresponding dispensing unit can be removed and replaced with a storage unit and dispensing unit corresponding to a different product (e.g., pads, over-the-counter medication, contraceptive products, etc.), where the dispensing unit is configured to hold and dispense the product from the storage unit and into the reception area.

Figure 7:
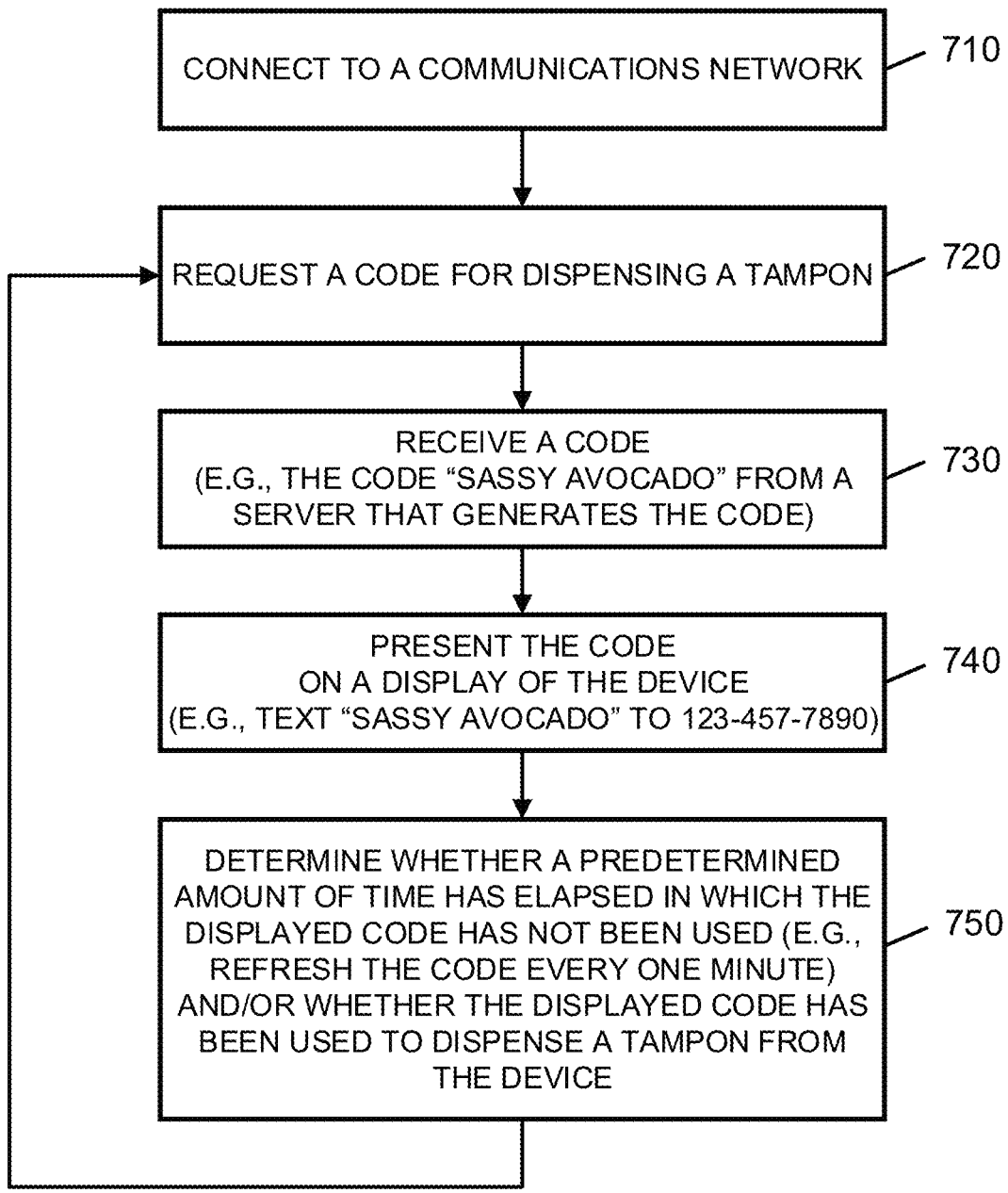
FIG. 7 shows an illustrative example of a process for operating a tampon dispensing device in which a code is presented on a display of the tampon dispensing device for receiving a tampon in accordance with some embodiments of the disclosed subject matter.

Turning to FIG. 7, an illustrative example of a process 700 for operating a tampon dispensing device in which a code is presented on a display of the tampon dispensing device for receiving a tampon is shown in accordance with some embodiments of the disclosed subject matter. In some embodiments, process 700 can be performed by any suitable device(s), such as a mobile device (e.g., a mobile phone, a tablet computer, a wearable computer, a laptop computer, and/or any other suitable mobile device) and/or a tampon dispensing device (e.g., as shown in and described above in connection with FIGS. 1-6). Note that, in some embodiments, the mobile device can be paired with the tampon dispensing device via any suitable communications link(s), such as BLUETOOTH, Wi-Fi, and/or any other suitable type of communications link(s).

Process 700 can begin at 710 by connecting to a communications network. In some embodiments, a mobile device that is connected to a tampon dispensing device (e.g., that has been installed on a wall of a public restroom) can input network information, such as wireless network information. For example, an administrative user, such as a facility manager, that has installed the tampon dispensing device on the wall of a public restroom can use a mobile device to input network information for connecting the tampon dispensing device to a local communications network. The network information can be transmitted to the tampon dispensing device, which uses the network information to associate with the wireless communications network. Additionally or alternatively, in some embodiments, the tampon dispensing device can connect to a communications network via a wired connection.

In some embodiments, the tampon dispensing device, upon being installed (e.g., on a wall of a public restroom) and upon being connected to a power source, can automatically connect to a local communications network.

In some embodiments, upon connecting the tampon dispensing device to a communications network, the tampon dispensing device can transmit device information to a server. For example, device information can include a unique device identifier associated with the tampon dispensing device, location information associated with the tampon dispensing device, etc.

At 720, the tampon dispensing device can request a code for dispensing a tampon. For example, the tampon dispensing device can, via a network interface, transmit a request to a server for a code. In another example, the controller of the tampon dispensing device can detect that the tampon dispensing device is in an active state and, in response to detecting that the tampon dispensing device is in an active state, the controller can transmit a request to a server associated with a tampon dispensing service for a code. In continuing this example, in response to authenticating the tampon dispensing device, the server can transmit a unique code to the tampon dispensing device.

Generally speaking, a server associated with a tampon dispensing service can generate a code for presenting on a display of a tampon dispensing device. As described below in connection with FIG. 9, in response to receiving a text message (or other suitable type of message) where the text message includes content matching the code presented on the display of the tampon dispensing device, the server can determine whether to transmit a dispense command or any other suitable instruction to the tampon dispensing device corresponding to the matching code (e.g., a dispense tampon command, an invalid code message, a try again later message, etc.). A more detailed example of a process for generating a code for dispensing a tampon is shown, for example, in FIG. 8.

Figure 8:
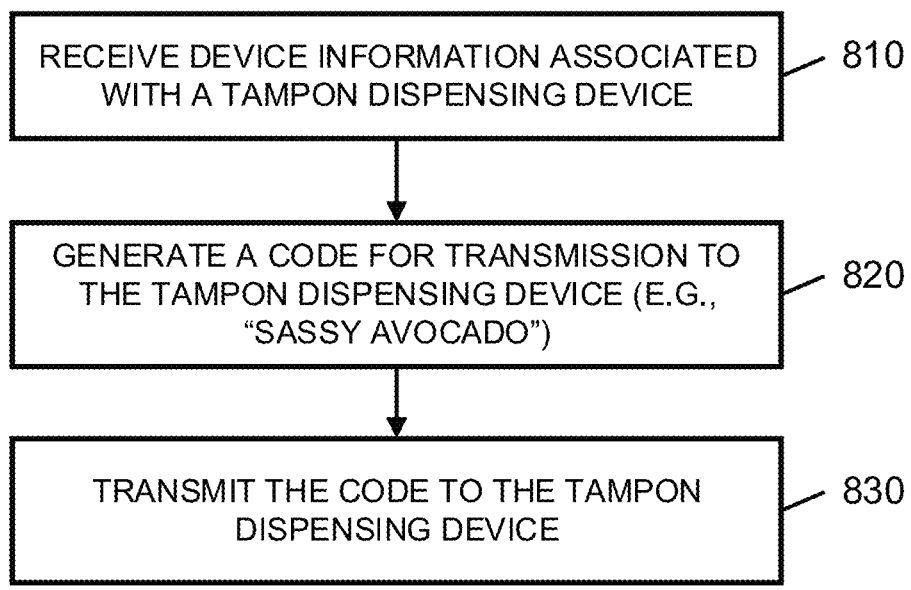
FIG. 8 show an illustrative example of a process for generating a code for transmission to a tampon dispensing device in accordance with some embodiments of the disclosed subject matter.

Turning to FIG. 8, an illustrative example 800 of a process for generating a code for transmission to a tampon dispensing device is shown in accordance with some embodiments of the disclosed subject matter. In some embodiments, blocks of process 800 can be executed by any suitable device, such as a server associated with a tampon dispensing service that dispenses tampons to users.

Process 800 can begin at 810 by receiving device information associated with a tampon dispensing device. For example, a server can receive a unique identifier associated with a tampon dispensing device. In another example, a server can receive a network identifier and a device name associated with the tampon dispensing device.

At 820, the server can generate a code for transmission to the tampon dispensing device having the unique identifier. For example, the server can generate a code that includes two terms, where the two terms are randomly selected from a list or dictionary of terms. In a more particular example, the server can generate a code "SASSY AVOCADO" in response to randomly selecting the term "SASSY" and randomly selecting the term "AVOCADO" from a term dictionary. In another more particular example, the server can generate the code by randomly selecting a term from a first dictionary and randomly selecting a term from a second dictionary. It should be noted that any suitable term dictionary can be used to generate the code.

In some embodiments, the server can determine whether the generated code is currently assigned to any tampon dispensing device. For example, in response to determining that the generated code is currently assigned (or has been previously assigned) to a tampon dispensing device.

In some embodiments, the server can store the code in a code database or any other suitable storage region in which the code is associated with a particular tampon dispensing device. In some embodiments, the code database can include multiple codes that have been associated with a particular tampon dispensing device (e.g., all codes associated with a tampon dispensing device, the last five codes that were associated with a tampon dispensing device, etc.). Alternatively, the code database can include the current code that is associated with a particular tampon dispensing device.

At 830, the server can transmit the code to a particular tampon dispensing device. For example, as described above, the server can transmit the code "SASSY AVOCADO" to controller 270 of a particular tampon dispensing device via a network interface.

It should be noted that, alternatively to process 800, the tampon dispensing device can include one or more term dictionaries and can select a code from the term dictionaries, where the controller can randomly select one or more terms from the term dictionaries as the code for presenting on the display. In continuing this example, the tampon dispensing device can transmit the code to a server of the tampon dispensing service for storage and association with the tampon dispensing service.

Referring back to FIG. 7, in response to receiving a code from the server, the tampon dispensing device can present the code on a display of the device at 740. For example, in response to receiving the code "SASSY AVOCADO," controller 270 of the tampon dispensing device can transmit the code to a display device, such as display 250, and instruct the display device to present the code along with instructions for dispensing a tampon. In a more particular example, the display device can be an electronic paper display that presents the code along with additional information that prompts a user of the tampon dispensing device to transmit a communication message that includes the code to a particular phone number in order to dispense a tampon from the tampon dispensing device (e.g., "TEXT the code SASSY AVOCADO to 123-456-7890 and receive a free tampon").

In some embodiments, the tampon dispensing device can determine whether the code being presented on the display of the tampon dispensing device is valid at 750.

For example, in some embodiments, the tampon dispensing device can determine whether a predetermined amount of time has elapsed in which the displayed code has not been used. In a more particular example, the code being presented on the display of the tampon dispensing device can be associated with a refresh time or a refresh rate (e.g., thirty seconds, one minute, five minutes, etc.). In response to determining that the particular amount of time has elapsed (e.g., the refresh rate of one minute has expired) in which a dispensing command has not been received, the tampon dispensing device can return to 720 and request an updated code for dispensing a tampon from the tampon dispensing device.

In another example, in some embodiments, the tampon dispensing device can determine whether the code being presented on the display of the tampon dispensing device has been used to dispense a tampon from the tampon dispensing device. In response to determining that a dispensing command has been received in connection with the currently presented code, the tampon dispensing device can return to 720 and request an updated code for dispensing the next tampon from the tampon dispensing device. Alternatively, the tampon dispensing device can be configured to automatically request an updated code for dispensing the next tampon from the tampon dispensing device in response to receiving a dispense instruction.

Figure 9:
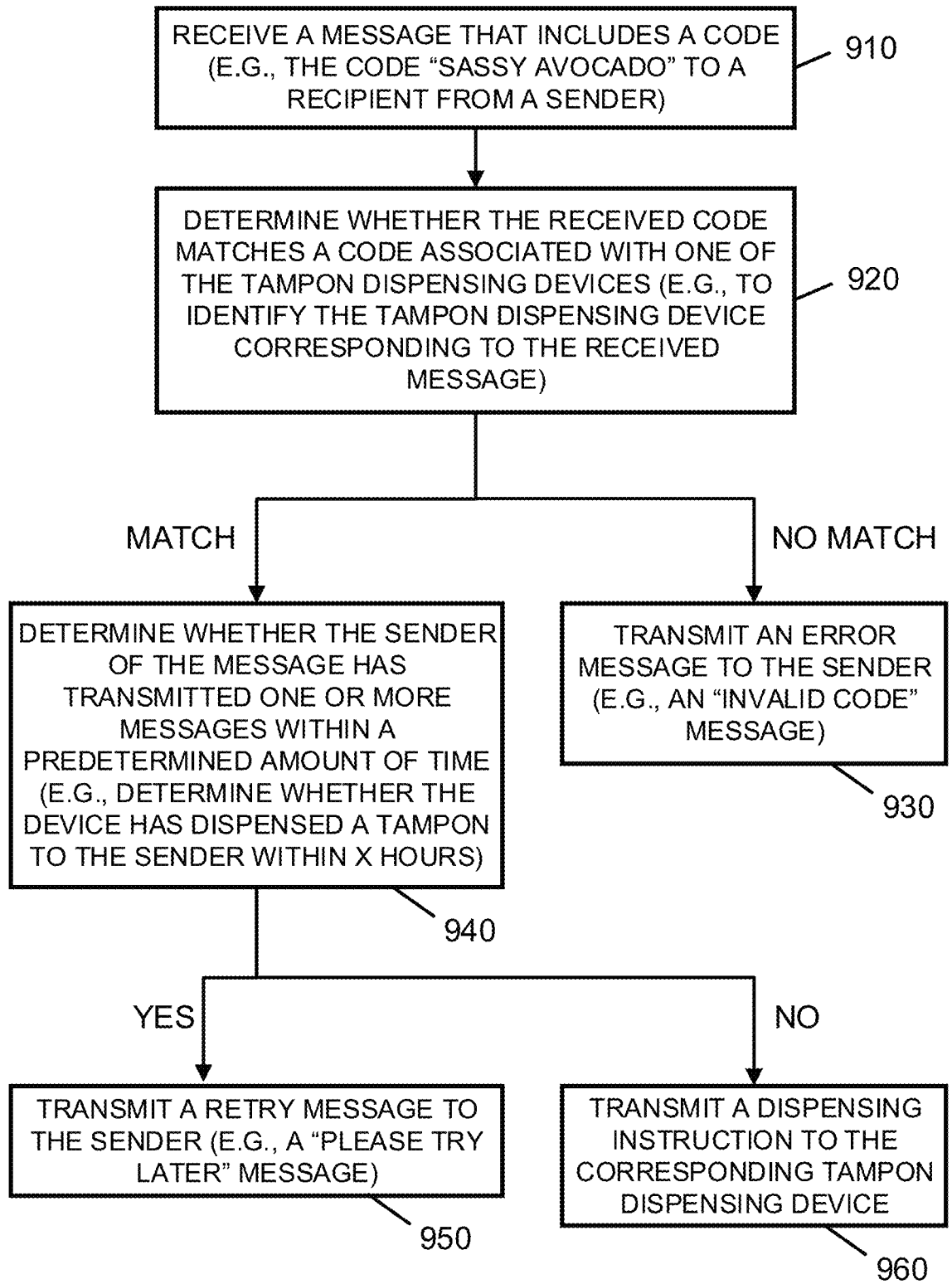
FIG. 9 shows an illustrative example of a process for determining whether a received code from a message matches a code associated with one of the tampon dispensing devices and determining whether to transmit a dispense instruction to a tampon dispensing device in accordance with some embodiments of the disclosed subject matter.

FIG. 9 shows an illustrative example of a process for determining whether a received code from a message matches a code associated with one of the tampon dispensing devices and determining whether to transmit a dispense instruction to a tampon dispensing device in accordance with some embodiments of the disclosed subject matter. In some embodiments, blocks of process 900 can be executed by any suitable device, such as a server associated with a tampon dispensing service that dispenses tampons to users.

Process 800 can begin at 910 by receiving a message that includes a code. For example, a server can receive a text message that includes the contents "SASSY AVOCADO." It should be noted that, although the embodiments described herein relate to the receipt of a text message in order to dispense a tampon from the tampon dispensing device, this is merely illustrative. The message can include any suitable type of communication, such as a text message, an e-mail, a chat and/or an instant message, a social networking post, and/or any other suitable type of message.

In response to receiving the message, the server can determine whether the received code matches a code associated with a tampon dispensing device at 920. For example, in some embodiments, in response to receiving a text message, the server can extract the contents of the text message to obtain the text "SASSY AVOCADO." In continuing this example, the server can then compare the text "SASSY AVOCADO" against a database of codes associated with one of multiple tampon dispensing devices. In determining that the received text "SASSY AVOCADO" corresponds with a code in the database of codes, the server can identify the particular tampon dispensing device from multiple tampon dispensing devices that corresponds with the received text message.

In response to determining that the code within the received message does not match a code being presented by any of the tampon dispensing devices, the server can transmit an error message to the message sender at 930. For example, the server can transmit a text message to the message sender that states "Sorry, but you sent an invalid code." In another example, the server can determine whether the code from the received message may correspond to a code in the database of codes and, in response to finding a similar code within a given similarity threshold, the server can transmit a text message to the message sender that states "Did you mean SASSY AVOCADO? If so, text "YES" and we will dispense a free tampon."

Alternatively, in response to determining that the code within the received message matches a code being presented by a tampon dispensing device, the server can determine whether the message sender has transmitted one or more similar messages within a predetermined amount of time at 940. For example, to inhibit a user of the tampon dispensing device from receiving multiple tampons within a given period of time, the server can determine whether a message sender (e.g., a particular mobile phone number, a particular username, etc.) has previously received a tampon within a particular period of time (e.g., one hour, five hours, one day, etc.). It should be noted that any suitable period of time can be used (e.g., a time threshold set by an administrative user, a time threshold set by the tampon dispensing service, etc.). It should also be noted that any suitable criterion can be used to determine whether a tampon should be dispensed—e.g., the same mobile phone number has transmitted a text message for a tampon within a particular period of time, the same mobile phone number has transmitted a text message for a tampon at the same tampon dispensing device within a particular period of time, etc.

In response to determining that the message sender has transmitted one or more messages to the tampon dispensing service within a predetermined amount of time (e.g., already requested a free tampon within the last thirty minutes), the server can transmit a retry message to the message sender at 950. For example, the server can transmit a responsive text message to the message sender that states "Please try again later." In another example, the server can transmit a responsive text message to the message sender regarding when another tampon will become available to the message sender—e.g., "Please try again in ten minutes."

Alternatively, in response to determining that the message sender has not transmitted one or more messages to the tampon dispensing service within a predetermined amount of time (e.g., the last requested tampon was more than thirty minutes ago), the server can transmit a dispensing instruction to the corresponding tampon dispensing device at 960. For example, upon determining that the code "SASSY AVOCADO" in a received text message corresponds with a particular tampon dispensing device and upon determining that the message sender is authorized to receive a tampon, the server can transmit a dispense command to the controller (e.g., controller 270) of the corresponding tampon dispensing device via its network controller.

Figure 10:
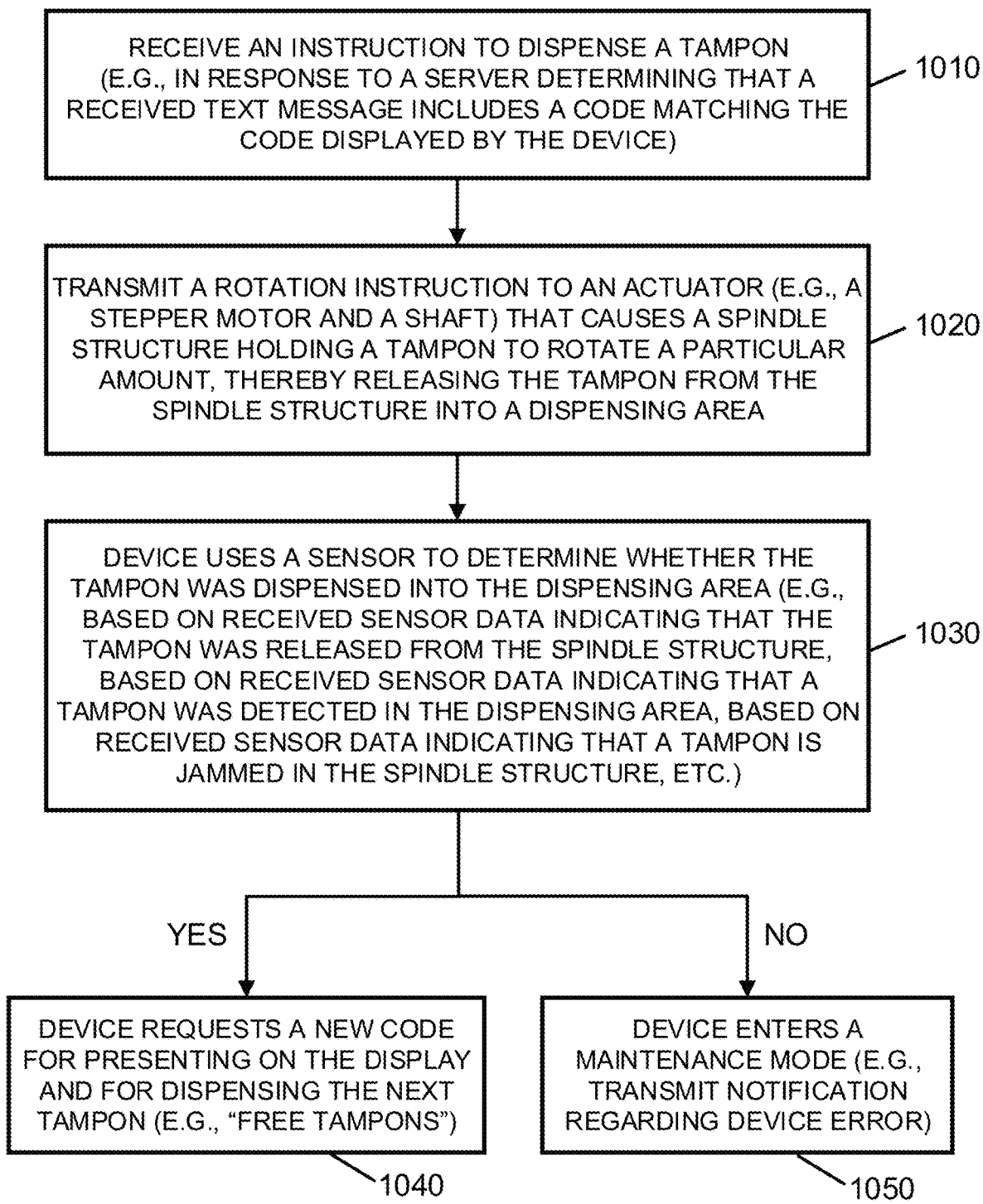
FIG. 10 shows an illustrative example of a process for operating a tampon dispensing device in which an actuator is used to move a spindle structure to dispense a tampon being held in the spindle structure to a reception area of the tampon dispensing device in accordance with some embodiments of the disclosed subject matter.

FIG. 10 shows an illustrative example of a process for operating a tampon dispensing device in which an actuator is used to move a spindle structure to dispense a tampon being held in the spindle structure to a reception area of the tampon dispensing device in accordance with some embodiments of the disclosed subject matter. In some embodiments, process 1000 can be performed by any suitable device(s), such as a tampon dispensing device (e.g., as shown in and described above in connection with FIGS. 1-6).

At 1010 of process 1000, the tampon dispensing device can receive a dispense command. For example, a controller of the tampon dispensing device can receive a dispense command or any other suitable instruction to dispense a tampon from a server (e.g., 960 of FIG. 9). In a more particular example, as described above, in response to receiving a text message from a mobile device of a user in which the text message includes a code that matches the code being presented on a display of the tampon dispensing device, the tampon dispensing device can receive a dispense command from a server that directs the controller of the tampon dispensing device to cause the tampon dispensing device to dispense an individual tampon into a reception area.

At 1020 of process 1000, in response to receiving the dispense command, the tampon dispensing device can transmit a rotation instruction to an actuator or other motion output components. As described above, in response to receiving an instruction to dispense a tampon, the controller can transmit an instruction that causes an actuator (e.g., a stepper motor connected to an actuator arm) to automatically rotate a spindle structure holding a tampon. It should be noted that the tampon dispensing device can include any suitable components to control the motion output components or actuator system, such as an instruction from a server to a controller, where the controller transmits the instruction to a stepper driver, the stepper driver transmits the instruction to a stepper motor controller, the stepper motor controller transmits the instruction to a stepper motor, and the stepper motor causes the spindle structure within the dispensing unit to move between different positions (e.g., an upward position that holds a tampon and a downward position that releases the tampon).

At 1030 of process 1000, the tampon dispensing device can determine whether the tampon was dispensed into a reception area for receipt by a user of the tampon dispensing device. For example, the tampon dispensing device can receive sensor data from one or more sensors to determine whether a tampon was properly dispensed from a storage unit holding multiple tampons through a dispensing unit that holds an individual tampon for dispensing and into a reception area. In a more particular example, the tampon dispensing device can include an infrared through-beam sensor having an emitter and a receiver or any other suitable photoelectric sensors, where the sensor can transmit an infrared light beam across a particular portion of tampon dispensing device that is suitable for detecting whether a tampon has been dispensed into a reception area by detecting beam disruptions. In continuing this example, one or more infrared through-beam sensors can be positioned at or near a reception area of the tampon dispensing device. In turn, the detection that the infrared light beam of the sensor has been disrupted can be correlated with an indication that a tampon has been dispensed into a reception area of the tampon dispensing device.

In response to the sensor data indicating that a tampon was dispensed into the reception area of the tampon dispensing device, the tampon dispensing device can transmit a request for a new code for presenting on the display so that a next tampon can be dispensed by the tampon dispensing device at 1040. For example, in response to detecting that a tampon was properly dispensed, the tampon dispensing device can prepare to dispense the next tampon—e.g., transmitting an actuation instruction that causes the spindle structure to return to its initial position in which the next tampon can be loaded into the spindle structure, transmitting a request to a server for an updated code for presentation on the display, adding to a counter that a tampon has been dispensed by the tampon dispensing device, monitoring the count of tampons in the storage unit of the tampon dispensing device, etc.

For example, in preparing the tampon dispensing device to dispense the next tampon, the tampon dispensing device can include additional sensors, such as a sensor that can detect whether a storage unit of the tampon dispensing device should be refilled or restocked. In a more particular example, an infrared through-beam sensor can be positioned within a storage unit such that, when a tampon is no longer disrupting the infrared light beam, the controller can use the sensor data to transmit a notification that the storage unit of the tampon dispensing device should be refilled. The notification can include, for example, an alert to an administrative user that states "There are less than five tampons left in the HOOHA™ on the first floor."

In response to the sensor data indicating that a tampon was not dispensed into the reception area of the tampon dispensing device, the tampon dispensing device can enter a maintenance mode at 1050. For example, in response to the sensor data indicating that a beam disruption has not been detected by the sensor within a particular period of time (e.g., one minute from the receipt of a dispense command), the tampon dispensing device can enter a maintenance mode in which the tampon dispensing device can transmit a notification to an administrative user, such as a facilities manager. The notification to the administrative user can include, for example, a push notification to a mobile application indicating that the tampon dispensing device requires the attention of the facilities manager. In another example, the notification to the administrative user can include error codes, sensor data, timestamp information, device information, etc.

Figure 11:
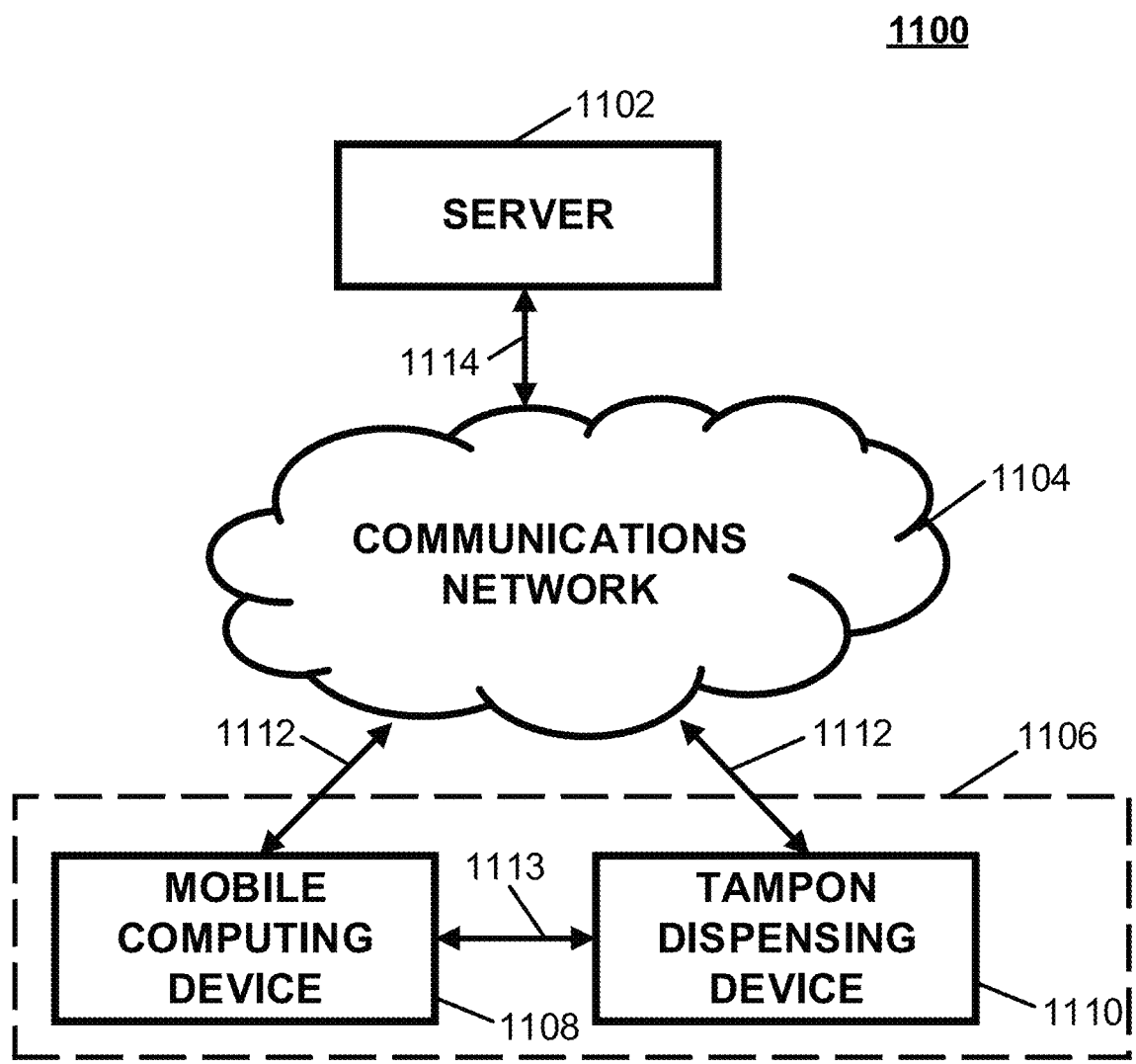
FIG. 11 shows a schematic diagram of an illustrative system suitable for implementation of mechanisms described herein for operating tampon dispensing devices in accordance with some embodiments of the disclosed subject matter.
Figure 12:
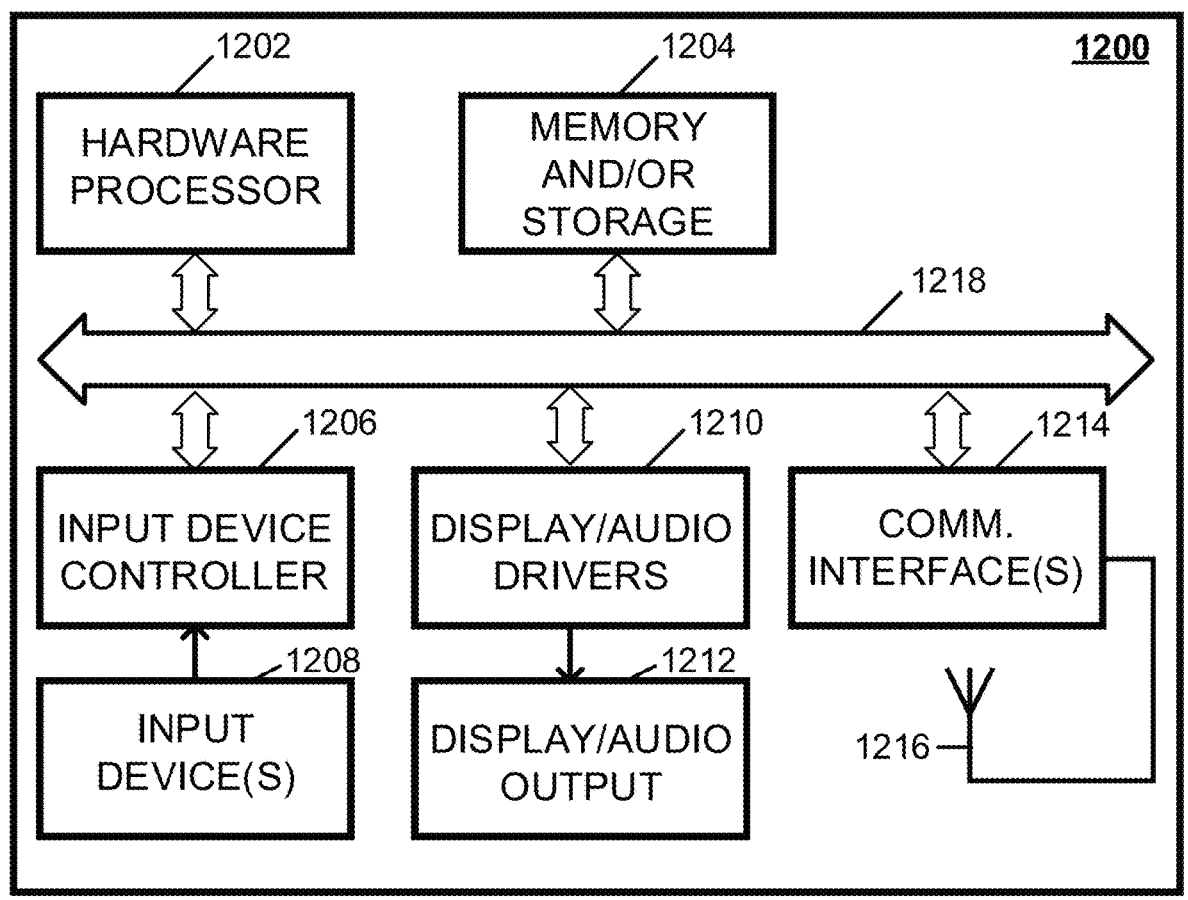
FIG. 12 shows a detailed example of hardware that can be used in a computing device of FIG. 11 in accordance with some embodiments of the disclosed subject matter.

Turning to FIG. 11, an illustrative example 1100 of hardware for operating tampon dispensing devices that can be used in accordance with some embodiments of the disclosed subject matter is shown. As illustrated, hardware 1100 can include a server 1102, a communications network 1104, and/or one or more devices 1106, such as mobile device 1108 and tampon dispensing device 1110.

Server 1102 can be any suitable server(s) for storing information (e.g., codes corresponding to tampon dispensing devices used to dispense a tampon, device information, network information, mobile device information, etc.), data, programs, and/or any other suitable content. In some embodiments, server 1102 can perform any suitable function(s). For example, in some embodiments, server 1102 can generate a code responsive to a request from a tampon dispensing device and can transmit the generated code to the tampon dispensing device for presentation on a display of tampon dispensing device 1110. As another example, in some embodiments, server 1102 can store information associated with a tampon dispensing device, such as a device identifier, network information, a code associated with the particular tampon dispensing device, and/or any other suitable device information. As yet another example, in some embodiments, server 1102 can store any suitable programs used to determine whether a code received in a message (e.g., a text message from a message sender) matches a code that is being presented by one of the tampon dispensing devices. As yet a further example, in some embodiments, server 1102 can storage any suitable programs used to determine whether the message sender should receive a tampon from a tampon dispensing device (e.g., whether the message sender sent a message for successfully receiving a tampon within a particular period of time).

Communications network 1104 can be any suitable combination of one or more wired and/or wireless networks in some embodiments. For example, communications network 1104 can include any one or more of the Internet, an intranet, a wide-area network (WAN), a local-area network (LAN), a wireless network, a digital subscriber line (DSL) network, a frame relay network, an asynchronous transfer mode (ATM) network, a virtual private network (VPN), and/or any other suitable communications network. Devices 1106 can be connected by one or more communications links (e.g., communications links 1112) to communications network 1104 that can be linked via one or more communications links (e.g., communications links 1114) to server 1102. The communications links can be any communications links suitable for communicating data among devices 1106 and server 1102, such as network links, dial-up links, wireless links, hard-wired links, any other suitable communications links, or any suitable combination of such links.

In some embodiments, mobile device 1108 can communicate with tampon dispensing device 1110 for any suitable purpose(s). For example, in some embodiments, mobile device 1108 can be used to configure a tampon dispensing device (e.g., a newly installed device on the wall in a public restroom), can be used to troubleshoot a tampon dispensing device (e.g., in response to receiving a notification that a tampon is jammed within the device, in response to receiving a notification that a storage unit of the tampon dispensing device should be refilled, etc.), etc. In some embodiments, mobile device 1108 can be any suitable type of mobile device, such as a mobile phone, a tablet computer, a wearable computer, a laptop computer, and/or any other suitable type of mobile device.

In some embodiments, mobile device 1108 can communicate with tampon dispensing device 1110 via one or more communications links (e.g., communications link 1113). In some embodiments, communications link 1113 can be any suitable type of communications link, such as BLUETOOTH, Wi-Fi, and/or any other suitable type of communications link.

In some embodiments, tampon dispensing device 1110 can be a device such as device 100 shown in and described above in connection with FIGS. 1-6.

Although server 1102 is illustrated as one device, the functions performed by server 1102 can be performed using any suitable number of devices in some embodiments. For example, in some embodiments, multiple devices can be used to implement the functions performed by server 1102.

Although one mobile device 1108 and one workout device 1110 are shown in FIG. 11 to avoid over-complicating the figure, any suitable number of mobile devices or tampon dispensing devices, and/or any suitable types of user devices, can be used in some embodiments. For example, tampon dispensing devices can be installed in each public restroom of a facility, where the tampon dispensing devices are associated with the same local communications network.

Server 1102 and user devices 1106 can be implemented using any suitable hardware in some embodiments. For example, in some embodiments, devices 1102 and 1106 can be implemented using any suitable general-purpose computer or special-purpose computer. For example, a mobile phone may be implemented using a special-purpose computer. Any such general-purpose computer or special-purpose computer can include any suitable hardware. For example, as illustrated in example hardware 1200 of FIG. 12, such hardware can include hardware processor 1202, memory and/or storage 1204, an input device controller 1206, an input device 1208, display/audio drivers 1210, display and audio output circuitry 1212, communication interface(s) 1214, an antenna 1216, and a bus 1218.

Hardware processor 1202 can include any suitable hardware processor, such as a microprocessor, a micro-controller, digital signal processor(s), dedicated logic, and/or any other suitable circuitry for controlling the functioning of a general-purpose computer or a special-purpose computer in some embodiments. In some embodiments, hardware processor 1202 can be controlled by a server program stored in memory and/or storage of a server, such as server 1102. In some embodiments, hardware processor 1202 can be controlled by a computer program stored in memory and/or storage 1204 of tampon dispensing device 1110.

Memory and/or storage 1204 can be any suitable memory and/or storage for storing programs, data, and/or any other suitable information in some embodiments. For example, memory and/or storage 1204 can include random access memory, read-only memory, flash memory, hard disk storage, optical media, and/or any other suitable memory.

Input device controller 1206 can be any suitable circuitry for controlling and receiving input from one or more input devices 1208 in some embodiments. For example, input device controller 1206 can be circuitry for receiving input from a touchscreen, from a keyboard, from one or more buttons, from a voice recognition circuit, from a microphone, from a camera, from an optical sensor, from an accelerometer, from a temperature sensor, from a near field sensor, from a pressure sensor, from an encoder, and/or any other type of input device.

Display/audio drivers 1210 can be any suitable circuitry for controlling and driving output to one or more display/audio output devices 1212 in some embodiments. For example, display/audio drivers 1210 can be circuitry for driving a touchscreen, a flat-panel display, a cathode ray tube display, a projector, a speaker or speakers, and/or any other suitable display and/or presentation devices.

Communication interface(s) 1214 can be any suitable circuitry for interfacing with one or more communications networks (e.g., computer network 1104). For example, interface(s) 1214 can include network interface card circuitry, wireless communication circuitry, and/or any other suitable type of communications network circuitry.

Antenna 1216 can be any suitable one or more antennas for wirelessly communicating with a communications network (e.g., communications network 1104) in some embodiments. In some embodiments, antenna 1216 can be omitted.

Bus 1218 can be any suitable mechanism for communicating between two or more components 1202, 1204, 1206, 1210, and 1214 in some embodiments.

Any other suitable components can be included in hardware 1200 in accordance with some embodiments.

In some embodiments, at least some of the above described blocks of the processes of FIGS. 7, 8, 9, and 10 can be executed or performed in any order or sequence not limited to the order and sequence shown in and described in connection with the figures. Also, some of the above blocks of FIGS. 7, 8, 9, and 10 can be executed or performed substantially simultaneously where appropriate or in parallel to reduce latency and processing times. Additionally or alternatively, some of the above described blocks of the processes of FIGS. 7, 8, 9, and 10 can be omitted.

In some embodiments, any suitable computer readable media can be used for storing instructions for performing the functions and/or processes herein. For example, in some embodiments, computer readable media can be transitory or non-transitory. For example, non-transitory computer readable media can include media such as non-transitory forms of magnetic media (such as hard disks, floppy disks, and/or any other suitable magnetic media), non-transitory forms of optical media (such as compact discs, digital video discs, Blu-ray discs, and/or any other suitable optical media), non-transitory forms of semiconductor media (such as flash memory, electrically programmable read-only memory (EPROM), electrically erasable programmable read-only memory (EEPROM), and/or any other suitable semiconductor media), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Accordingly, tampon dispensing devices and methods for using the same are provided.

Although the invention has been described and illustrated in the foregoing illustrative embodiments, it is understood that the present disclosure has been made only by way of example, and that numerous changes in the details of implementation of the invention can be made without departing from the spirit and scope of the invention. Features of the disclosed embodiments can be combined and rearranged in various ways.

What is claimed is:

1. A tampon dispensing device comprising:
a display that presents one or more codes for receiving a tampon;
an actuator that is connected to a spindle structure that dispenses the tampon from a plurality of tampons stored in a storage unit; and
a controller that is connected to the display and the actuator, wherein the controller is configured to:
receive, from a server, a code for dispensing one of the plurality of tampons;
present the received code on the display;
receive, from the server, a request to dispense one of the plurality of tampons from the storage unit; and
transmit an instruction to the actuator that causes the actuator to rotate a spindle structure such that the tampon is dispensed from the storage unit into a dispensing area.

2. The tampon dispensing device of claim 1, wherein the display is an electronic paper display.

3. The tampon dispensing device of claim 1, wherein the received code is a phrase comprising a plurality of words.

4. The tampon dispensing device of claim 1, wherein the controller is further configured to present the received code and a phone number for transmitting the received code to dispense one of the plurality of tampons.

5. The tampon dispensing device of claim 1, wherein the actuator further comprises a stepper motor that is connected to a drive shaft, wherein the drive shaft is connected to the spindle structure that is holding the tampon, wherein the instruction causes the stepper motor to rotate the drive shaft by a particular rotation amount, and wherein the rotation of the draft shaft causes the spindle structure to rotate to dispense the tampon from the spindle structure to the dispensing area.

6. The tampon dispensing device of claim 1, wherein the drive shaft is connected to a central portion of the spindle structure.

7. The tampon dispensing device of claim 1, wherein the spindle structure includes a recessed portion for receiving an individual tampon from the storage unit.

8. The tampon dispensing device of claim 7, further comprising a funnel between the storage unit and the dispensing area, wherein the funnel includes the spindle structure and one or more aligners that cause the individual tampon to be placed from the storage unit to the recessed portion of the spindle structure.

9. The tampon dispensing device of claim 7, further comprising a funnel between the storage unit and the dispensing area, wherein the funnel includes the spindle structure and one or more aligners that cause the individual tampon to be released from the recessed portion of the spindle structure to the dispensing area.

10. The tampon dispensing device of claim 1, further comprising a door that includes a window for viewing at least a portion of the plurality of tampons in the storage unit.

11. The tampon dispensing device of claim 1, further comprising a network interface that is connected to the controller, wherein the controller is further configured to:
   transmit, to the server via the network interface, a request for the code to dispense one of the plurality of tampons; and
   receive, from the server via the network interface, the code responsive to the request.

12. The tampon dispensing device of claim 11, wherein the controller is further configured to detect that the device is in an active state and, in response to detecting that the device is in the active state, the request for the code is transmitted to the server via the network interface.

13. The tampon dispensing device of claim 11, wherein the controller is further configured to determine that a predetermined amount of time has elapsed in which one of the plurality of tampons has not been dispensed and transmit a request to the server for an updated code to present on the display for dispensing one of the plurality of tampons.

14. The tampon dispensing device of claim 11, wherein the controller is further configured to transmit a request to the server for an updated code to present on the display for dispensing a next tampon from the plurality of tampons in response to dispensing the tampon from the storage unit into the dispensing area.

15. The tampon dispensing device of claim 1, further comprising a sensor that detects whether the tampon was dispensed from the storage unit into the dispensing area, wherein the sensor is connected to the controller and wherein the controller is further configured to determine whether the tampon was properly dispensed into the dispensing area based on sensor data from the sensor.

16. The tampon dispensing device of claim 15, wherein the controller is further configured to transmit an alert notification in response to determining that the tampon was not properly dispensed.

17. The tampon dispensing device of claim 15, wherein the controller is further configured to enter a maintenance mode in which device error information that at least includes the sensor data is transmitted to a maintenance account.

18. The tampon dispensing device of claim 15, wherein the sensor is a through-beam sensor that emits a beam within the dispensing area of the tampon dispensing device.

19. The tampon dispensing device of claim 1, further comprising a sensor that detects whether the plurality of tampons stored in the storage unit is less than a predetermined amount, wherein the sensor is connected to the controller and wherein the controller is further configured to transmit an alert notification in response to determining that the plurality of tampons stored in the storage unit is less than the predetermined amount.

20. The tampon dispensing device of claim 19, wherein the sensor is a through-beam sensor that emits a beam at a particular level within the storage unit of the tampon dispensing device.

* * * * *